United States Patent [19]

Tepic

[11] Patent Number: 4,938,774
[45] Date of Patent: Jul. 3, 1990

[54] DYNAMIC SELF-LOCKING STEM FOR HIP PROSTHESIS

[75] Inventor: Slobodan Tepic, Davos, Switzerland

[73] Assignee: Laboratorium für experimentelle Chirurgie, Davos, Switzerland

[21] Appl. No.: 335,782

[22] PCT Filed: Aug. 15, 1987

[86] PCT No.: PCT/EP87/00451
§ 371 Date: Mar. 22, 1989
§ 102(e) Date: Mar. 22, 1989

[87] PCT Pub. No.: WO89/01321
PCT Pub. Date: Feb. 23, 1989

[51] Int. Cl.$^5$ .......................... A61F 2/36; A61F 2/30; A61F 2/28
[52] U.S. Cl. ......................................... 623/23; 623/16; 623/18
[58] Field of Search ............................... 623/16, 18–23

[56] References Cited

U.S. PATENT DOCUMENTS 4,792,339 12/1988 Tepi .................................. 623/18 X

FOREIGN PATENT DOCUMENTS

WO86/06954 12/1986 PCT Int'l Appl. .................. 623/18

Primary Examiner—Ronald L. Frinks
Attorney, Agent, or Firm—Walter C. Farley

[57] ABSTRACT

The stem for joint prostheses, in particular for hip prosthesis, has a proximal neck region (1), a lateral tension region (2), a medial compression region (3) and a central region (4) lying between said lateral and medial regions (2,3). The central region (4) is provided with a regular pattern of anteroposterior cuts (5) extending from said proximal region (1) to the distal end (6) of the stem rendering the stem stiffness adaptable to the stiffness of the receiving bone cavity.

9 Claims, 2 Drawing Sheets

DYNAMIC SELF-LOCKING STEM FOR HIP PROSTHESIS

This application corresponds to application No. PCT/EP87/00451 filed Aug. 15, 1987 under the provisions of the Patent Cooperation Treaty and the benefit of the priority of said application is claimed.

This invention relates to a stem for joint prostheses, in particular for hip prosthesis, having a proximal neck region and, a lateral tension region, a medial compression regions a central region lying between said lateral and medial region.

Prosthetic loosening remains a major complication in the replacement of joints, testifying to the still unresolved problems of interfacing load-bearing implants to living bone. Necessary conditions for sound long-term anchorage of a joint prothesis are:

- appropriate load transfer between the prothesis and bone; and
- a motion-free interface between the prosthesis and bone.

Bone as a living tissue sets these conditions which must be respect in the design of prosthetic devices.

Femoral component anchorage in hip joint replacements by a stem has probably been responsible for their generally superior performance to any other prosthetic component to date. Elimination of bone cement from the stem anchorage makes the above requirements even more critical and more difficult to fulfill even in this rather simple rod-in-tube configuration.

Summary of the Invention

The invention solves the problem of how to design a dynamic self-locking stem for a joint prosthesis capable of adapting its stiffness to the stiffness of the surrounding bone tissue.

The stem according to the invention is unique in that
- it has a structure to facilitate load transfer from prosthesis to bone;
- it has a mechanism to ensure a motion-free interface with bone;
- it is adaptive and will accomodate the unavoidable bone response to the new mechanical environment.

The advantages offered by the invention are the result of the design modifications within the stem in contrast to the conventional surface changes on the stem of most state of the art prosthesis. Each of the medial and lateral regions can be shaped and sized appropriately for its function, allowing gradual load transfer to bone, i.e. the compliance of said medial and lateral regions can be fully matched to that of bone cortices. This provides the basis for the structural design, whereas the segments between said lateral and medial regions are used to control the interface stresses. The connections between said medial/lateral regions and said segments consist of very thin flexible bridges that act as hinges. Inclinations of the segments with respect to the stem axis determines the amount of stem widening that occurs with loading. With physiological loading the lateral region tends to move proximally as the medial region moves distally and the segments turn so as to increase the separation of the medial/lateral regions. The optimal design criterion calls for stem widening at all levels producing sufficient normal interface stress to prevent any movement due to shear stress. This guarantees absolute dynamic stability at the bone-prosthesis interface.

The bending stiffness of the stem depends on the amount of shear coupling provided to the medial and lateral regions of the stem by bone. Assuming a stable bone-prosthesis interface, the stiffness of the stem will increase with the increase in stiffness of surrounding bone. Modulation of stem stiffness by bone stiffness plays an important role in bone reaching an equilibrium state following stem insertion.

Any stem will "stress shield" some bone within the load transfer zone. Generally, a higher stem stiffness/bone stiffness ratio results in more stress shielding. This results in reduced bone stiffness, amplifying the stress shielding effect. The result of this positive feedback process would be total stress shielding of affected bone. The stem stiffness modulation by bone avoids this effect since reduced bone stiffness caused by stress shielding will also soften the stem.

In addition to the unique features discussed above, the stem according to the invention offers an important practical advantage of immediate stability. At insertion, the stem is hammered in through an anvil, directing the insertion force latero-distally. This causes the stem to reduce the width and elastically preload the interface with the bone. This preload will eventually be released through bone remodelling and will not provide lasting stability. This preload allows bone apposition against the stem and thus improves the quality of fit. Good fit between the stem and bone is required for the locking mechanism to function as described above.

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

Description of the Preferred Embodiments

Figure 1:
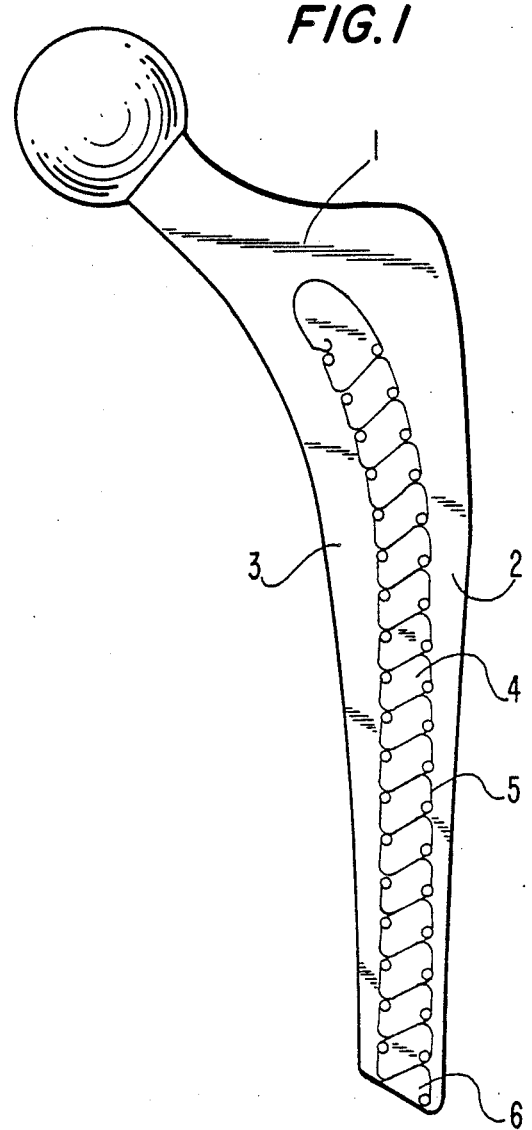
FIG. 1 is an antero-posterior view of a stem according to the invention.

FIG. 1 represents a stem according to the invention. Lateral region 2 of the stem is separated from the medial region 3 by a multitude of full-thickness cuts 5 running down the middle region 4 of the stem from the proximal region 1 out to the distal end 6 of the stem. Cuts 5 are preferably produced by spark erosion wire cutting.

Figure 2:
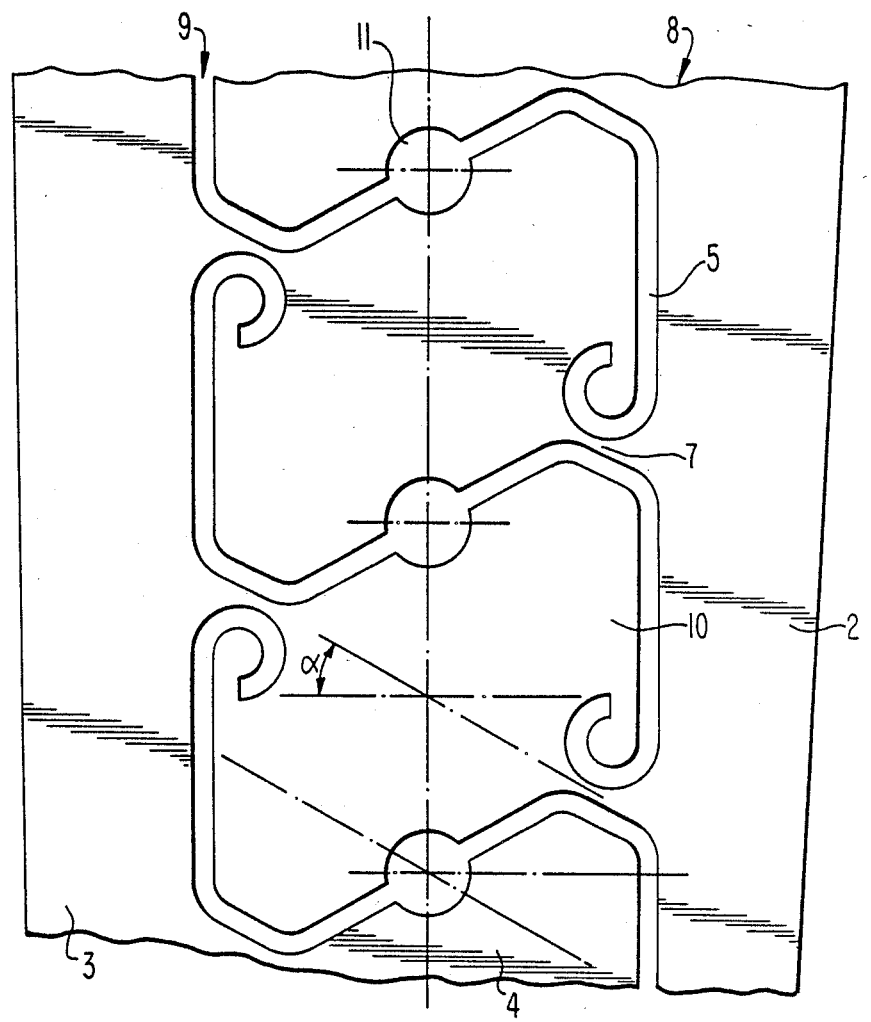
FIG. 2 is an enlarged sectional view of the middle segment of the stem according to FIG. 1.

FIG. 2 represents an enlarged middle segment of the stem according to FIG. 1. Tension transferring lateral truss 2 and compression transferring medial truss 3 are separated from the middle region 4 by sections of the cuts 5 running along lines 8 and 9 respectively. Thin flexible hinges 7 are connecting segments 10 to the trusses 2 and 3. The line connecting the hinges of one segment is inclined with respect to the transverse axis by an angle a, which is between 20° and 40°, preferably between 25° and 35°. A cutting wire is inserted through the holes 11 and then guided for cutting along a generally sinuous S- or Z-shaped trajectory 5.

The distance between hinges in the proximodistal direction is between 6 and 10 mm, preferably between 7 and 9 mm.

I claim:

1. A stem for joint prosthesis, in particular for hip prosthesis, of the type having a proximal neck region (1), a lateral tension region (2), a medial compression region (3), and a central region (4) lying between said lateral and media regions (2, 3), characterized in that said central region (4) includes means defining a regular pattern of sinuous anteroposterior cuts (5), each said cut having two distinct ends, said pattern of cuts extending from said proximal region (1) to the distal end (6) of the stem, rendering the stem stiffness adaptable to the stiffness of the receiving bone cavity, said cuts being arranged in such a way that a series of flexible hinges (7) is formed along boundaries (8, 9) of said lateral and medial regions (2, 3) with said central portion (4) of the stem allowing movement of mediolateral segments (10) formed by said cuts (5).

2. A stem according to claim 1, characterized in that said cuts (5) are in the shape of a Z.

3. A stem according to claim 2, characterized in that the angle formed by the line connecting the hinges (7) of one segment (10) and the transverse axis of the stem, varies along the stem producing sufficient compression between the stem and bone to prevent movement at the interface.

4. A stem according to claim 3 characterized in that said angle is between about 20° and about 40°.

5. A stem according to claim 4 characterized in that the distance between said hinges (7) in proximodistal direction is between 6 and 10 mm.

6. A stem according to claim 4 wherein said angle is between about 25° and 35°.

7. A stem according to claim 5 wherein said distance between said hinges is between 7 and 9 mm.

8. A stem according to claim 1 characterized in that the angle formed by a line connecting the hinges (7) of one segment (10) and the transverse axis of the stem varies along the stem producing sufficient compression between the stem and bone to prevent movement at the interface.

9. A stem for joint prosthesis of the type having a proximal neck region (1), a lateral tension region (2), a medial compression region (3) and a central region (4) lying between said lateral and medial regions (2, 3), comprising means in said central region (4) defining a repetitive series of generally sinuous, narrow, anteroposterior cuts (5), each said cut having two distinct ends, said series of cuts extending from said proximal region (1) to the distal end (6) of the stem, said cuts defining therebetween a plurality of mediolateral segments (10) and a series of flexible hinges (7) connecting opposite sides of said mediolateral segments to said lateral and medial regions, respectively, along boundaries (8, 9) of said lateral and medial regions rendering the stem stiffness adapatable to the stiffness of the receiving bone cavity, said cuts being arranged in such a way that said flexible hinges (7) allow limited movement of said mediolateral segments (10) formed by said cuts (5).

* * * * *